United States Patent
Mertens et al.

(10) Patent No.: US 7,014,827 B2
(45) Date of Patent: Mar. 21, 2006

(54) SYNTHESIS OF SILICOALUMINOPHOSPHATES

(76) Inventors: Machteld Maria Mertens, Beringstraat 72, Boortmeerbeek (BE), 3190; Brita Engels, Gelegstraat 9, Betekom (BE), 3130

( * ) Notice: Subject to any disclaimer, the term of this patent is extended or adjusted under 35 U.S.C. 154(b) by 16 days.

(21) Appl. No.: 10/002,241

(22) Filed: Oct. 23, 2001

(65) Prior Publication Data

US 2003/0078159 A1 Apr. 24, 2003

(51) Int. Cl.
- C01B 25/36 (2006.01)
- B01J 27/00 (2006.01)
- C07C 1/02 (2006.01)

(52) U.S. Cl. .............. 423/305; 423/306; 423/328.2; 502/210; 502/214; 502/439; 585/640

(58) Field of Classification Search ............ 423/305, 423/306, 328.2, DIG. 30; 502/210, 214, 439; 585/640
See application file for complete search history.

(56) References Cited

U.S. PATENT DOCUMENTS

| | | | |
|---|---|---|---|
| 4,440,871 A | 4/1984 | Lok et al. | 502/214 |
| 4,861,743 A | 8/1989 | Flank et al. | 502/214 |
| 5,013,535 A | 5/1991 | Bedard et al. | 423/277 |
| 5,096,684 A | 3/1992 | Guth et al. | 423/306 |
| 5,126,308 A | 6/1992 | Barger et al. | 502/214 |
| 5,143,879 A | 9/1992 | Whitehurst | 502/85 |
| 5,296,208 A | 3/1994 | Lesch | 423/700 |
| 5,744,680 A * | 4/1998 | Mulvaneyl et al. | 585/640 |
| 6,111,037 A | 8/2000 | Auburn et al. | |
| 6,121,503 A * | 9/2000 | Janssen et al. | 585/640 |
| 6,160,191 A | 12/2000 | Smith et al. | |

FOREIGN PATENT DOCUMENTS

| | | |
|---|---|---|
| WO | WO 98/15496 | 4/1998 |
| WO | WO 99/19254 | 4/1999 |
| WO | WO 01/25151 | 4/2001 |
| WO | WO 01/47810 | 7/2001 |

* cited by examiner

*Primary Examiner*—Stanley S. Silverman
*Assistant Examiner*—Maribel Medina

(57) ABSTRACT

Disclosed is a method for the manufacture of silicoaluminophosphate (SAPO) and/or aluminophosphate (ALPO) molecular sieves. The method includes maintaining the slurry of the as crystallized molecular sieve under substantially static conditions when stored after substantially complete crystallization and prior to recovery of the product.

22 Claims, No Drawings

SYNTHESIS OF SILICOALUMINOPHOSPHATES

FIELD OF THE INVENTION

The present invention relates to a process for the synthesis and recovery of silicoaluminophosphate (SAPO) and/or aluminophosphate (ALPO) molecular sieves and mixtures thereof. In particular the invention is directed to the storage conditions for the molecular sieve after formation by crystallization and before recovery.

BACKGROUND OF THE INVENTION

Silicoaluminophosphates (SAPOs) and aluminophosphates (ALPOs), are important classes of molecular sieve and have been used as adsorbents and catalysts. As catalysts, SAPOs and ALPOs have been used in processes such as fluid catalytic cracking, hydrocracking, isomerization, oligomerization, the conversion of alcohols or ethers, and the alkylation of aromatics. In particular, the use of SAPOs and ALPOs in converting alcohols or ethers to olefin products, particularly ethylene and propylene, is becoming of greater interest for large scale, commercial production facilities. In this regard silicoaluminophosphates are favoured catalysts for the conversion of oxygenates to olefins with SAPO-34 being of particular importance.

It has been recognised for some time that SAPO and ALPO molecular sieves are relatively difficult to manufacture. SAPO and ALPO synthesis procedures are particularly sensitive to small variations in the composition of the reaction mixture and the conditions used. The problems associated with the synthesis of these molecular sieves are exacerbated by the generally low yields of crystalline material obtained from the synthesis process. These difficulties contribute to the relatively high cost of SAPO and ALPO molecular sieves.

There have been varying attempts in the art to improve the yield of SAPO and ALPO molecular sieves. U.S. Pat. No. 5,296,208 describes a process for the synthesis of crystalline molecular sieve materials including SAPO and ALPO molecular sieves. The process described therein requires the removal of at least some of the nitrogen-containing organic templating agent from the reaction mixture during the crystallization process. This removal has the effect of increasing the final yield of crystalline molecular sieve.

PCT Publication No. WO 01/25151 describes a process for the synthesis of SAPO molecular sieves in which the pH of the synthesis mixture is adjusted during the synthesis. The control of pH in this process results in an improved yield of SAPO molecular sieve.

A further difficulty encountered with SAPO and ALPO molecular sieves is their relative instability in the synthesis mixture once the crystallization reaction is completed. If these materials remain in the synthesis solution for any period of time after the reaction is completed they are prone to dissolution back into the reaction mixture. This effect further reduces the yield of these molecular sieves. This is an important problem in the preparation of SAPO and ALPO molecular sieves as it is often necessary to retain the crystallized molecular sieve within the reaction mixture as a slurry after completion of the crystallization for extended periods of time prior to transfer of the slurry to the recovery stage of the synthesis.

The problem of SAPO and ALPO dissolution is recognised in the art and various solutions have been proposed to reduce this problem in U.S. Pat. No. 5,296,208. One solution proposed is to remove organic templating agent prior to cooling of the reaction mixture. A further proposed solution is the rapid dilution of the reaction mixture with relatively large amounts of water on completion of the reaction. Another proposed solution is the rapid and significant decrease in temperature on completion of the reaction.

There is a need for alternative synthetic processes, which address the problem of SAPO and ALPO dissolution upon storage prior to recovery after completion of crystallization.

SUMMARY OF THE INVENTION

In general, this invention provides a process for the synthesis of crystalline molecular sieve wherein the molecular sieve is one or more silicoaluminophosphates (SAPO), and/or one or more aluminophosphate (ALPO) and mixtures thereof, which process comprises,
 a) forming a reaction mixture comprising a source of alumina or aluminum, a source of phosphate, at least one nitrogen-containing organic templating agent, and optionally a source of silica;
 b) inducing crystallization of crystalline molecular sieve from the reaction mixture to form a slurry comprising crystalline molecular sieve; and
 c) recovering crystalline molecular sieve from the slurry, wherein during any period of time after substantial completion of the crystallization in step (b) and prior to the step of recovery (c), the slurry is held under substantially static conditions.

DETAILED DESCRIPTION OF THE INVENTION

The present invention relates to a process for the synthesis and recovery of silicoaluminophosphate (SAPO) and/or aluminophosphate (ALPO) molecular sieves and mixtures thereof. In particular, the invention is devoted to a process for the manufacture of such molecular sieves where the problems of loss of crystalline material, particularly in storage, is significantly alleviated. The present invention addresses the situation when the slurry must be stored before recovery of the crystalline molecular sieve product. By storage is meant that the slurry obtained at substantial completion of the crystallization step is; either retained in the crystallization vessel for a period of time prior to the recovery stage; or is removed from the crystallization vessel and stored in a separate vessel for a period of time prior to the recovery stage; or a combination of these.

The process of this invention begins by forming a reaction mixture comprising a source of alumina, a source of phosphate, at least one nitrogen-containing organic templating agent and, optionally, a source of silica.

The source of silica may be a silicate, e.g., fumed silica, such as Aerosil (available form Degussa), a tetraalkyl orthosilicate, or an aqueous colloidal suspension of silica, for example one sold by E. I. du Pont de Nemours, Wilmington, Del., under the tradename Ludox. Examples of sources of alumina include aluminum alkoxides such as aluminum isopropoxide, aluminum phosphates, aluminum hydroxide, sodium aluminate, and pseudoboehmite. Examples of sources of phosphate include phosphoric acid, organic phosphates such as triethyl phosphate, and aluminophosphates.

The nitrogen-containing organic templating agent, also called template, may be chosen from the group consisting of tetraethyl ammonium compounds, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium compounds, dipropylamine, and mixtures thereof. The tetraethylammonium compounds include tetraethyl ammonium hydroxide (TEAOH), tetraethyl ammonium phosphate, tetraethyl ammonium fluoride, tetraethyl ammonium bromide, tetraethyl ammonium chloride, and tetraethyl ammonium acetate. Preferred tetraethyl ammonium compounds are tetraethyl ammonium hydroxide and tetraethyl ammonium phosphate. In one embodiment, the SAPO and ALPO molecular sieve structure can be effectively controlled using combinations of templates. For example, the SAPO molecular sieve is manufactured using a template combination of TEAOH and dipropylamine.

The reaction mixture is obtained by mixing the sources of alumina, phosphorus, nitrogen-containing organic templating agent. Crystallization is then induced. The amounts of reagents, method of preparing the reaction mixture and crystallization conditions depend on the particular molecular sieve being prepared and follow those of the methods generally known in the art. See for example, U.S. Pat. Nos. 4,440,871; 4,861,743; 5,096,684; and 5,126,308, the methods of making of which are fully incorporated herein by reference.

Crystallization is induced by submitting the reaction mixture to hydrothermal treatment. This is advantageously performed at temperatures within the range of from 80° C. to 250° C., preferably from 125° C. to 225° C., more preferably between 150° C. and 180° C. Temperature may be increased gradually or stepwise, during treatment. Heat is applied for a period of time effective to form the crystalline molecular sieve. Formation of the crystalline molecular sieve can take anywhere from about 30 minutes up to as much as two or more weeks. Preferably heat is applied for a duration of between 45 minutes to 240 hours, more preferably between 1 and 120 hours. The duration depends on the temperature applied. Typically, higher temperatures require smaller hydrothermal durations.

The silicoaluminophosphate synthesis may be aided by seeds form a previous synthesis or by seeds of another molecular sieve. Hydrothermal treatment may be carried out with or without agitation, for example stirring or tumbling (rotating the vessel about a horizontal axis), but is preferably carried out with agitation.

One preferred method for the crystallization stage in the process of the present invention is described in U.S. Pat. No. 5,296,208, which is fully incorporated herein by reference. Broadly this process comprises the following: forming an aqueous reaction mixture suitable for the hydrothermal production of a crystalline molecular sieve that contains at least one nitrogen-containing organic templating agent and optionally a supplemental organic base, the organic base which includes templating agent being in excess of the amount to be incorporated within the product molecular sieve crystals; establishing a crystallization period by heating and maintaining the reaction mixture at a crystallization temperature of at least 100° C. to from crystals of the molecular sieve product and establish an equilibrium between molecular sieve crystal formation and molecular sieve dissolution; and thereafter, removing at least some of the excess organic base during the course of the crystallization period whereby the equilibrium between product formation and product dissolution of the reaction system is shifted in favor of decreased dissolution of molecular sieve product at the existing temperature conditions; and recovering the crystallized molecular sieve product from the reaction mixture.

Another preferred method for the crystallization stage in the process of the present invention is as described in PCT Publication No. WO 01/47810, which is fully incorporated herein by reference, and in which process agitation by stirring is used in a discontinuous fashion during the crystallization stage. Thus in the process of the present invention stirring may be utilized during the crystallization stage for between 20 to 90%, and preferably 30 to 80% of any period where heat is applied. The process of the present invention may also be undertaken with agitation throughout the crystallization stage.

A key aspect of the present invention is that the slurry obtained after substantial completion of the crystallization is maintained under specific conditions whilst being stored ready for recovery. The dissolution of crystalline molecular sieve during storage is considerably reduced by storing the slurry under substantially static conditions as hereinafter defined.

In the context of the present invention it is important to recognize that by the term static is meant that the slurry is un-stirred, not tumbled or agitated in any way during storage and by substantially static conditions is meant the absence of high impact agitation throughout the period of storage. High impact agitation includes the level of agitation normally required during the crystallization stage for extended periods to maintain the reaction mixture as a homogeneous or quasi-homogeneous phase. In one embodiment the slurry may be stored under completely undisturbed conditions until it is transferred to the recovery phase of the process. However, it should be recognized that during the storage process it may be necessary to impart some form of limited agitation to the slurry ideally for short periods of time in order to ensure that the molecular sieve crystals do not compact during storage. This limited agitation may be imparted through the agitation means used during the crystallization process; this form of agitation would be imparted for a short period of time during the substantially static phase. In a preferred embodiment the slurry is stored under static conditions.

When the period of the substantially static phase is predetermined, then by short period of time is meant a period, which is 20% or less of the substantially static phase, preferably 15% or less of the substantially static phase and most preferably 10% or less of the substantially static phase. When the period of the substantially static phase is not pre-determined, then by short period of time is meant a period of 12 minutes or less in any one hour of the substantially static phase, preferably 9 minutes or less in any one hour of the substantially static phase and most preferably 6 minutes or less in any one hour of the substantially static phase. These periods of time may be continuous or separate periods of agitation. Thus by way of example it is possible to maintain the slurry under static conditions for 8 minutes followed by a of 2 minute period of agitation, which is then followed by a further 8 minute period under static conditions, and so on until recovery of the crystalline molecular sieve from the slurry. These short periods of agitation whilst not being predetermined in duration may be determined by the prevailing conditions of the slurry during storage with agitation being applied intermittently as and when needed. The need for agitation may arise if the crystalline molecular sieve material has settled to the bottom of the crystallization vessel or storage vessel during storage and is in danger of becoming compacted in this state; in this situation enough agitation may be applied to re-disperse the crystalline molecular sieve material. These short periods of agitation are especially required when the agitation used during the substantially static phase is relatively high impact. It is envisaged in a further embodiment that the substantially static phase may comprise continuous low impact agitation. By low impact agitation is meant agitation insufficient to provide a homogeneous or quasi-homogenous phase similar to that observed during the crystallization phase. This lack of a homogeneous or quasi-homogeneous phase is clearly observable when the major components of the reaction mixture are immiscible such as for example when the nitrogen-containing organic templating agent is immiscible with the aqueous reaction solvent. In this scenario the low impact agitation is such that it does not significantly re-constitute the homogeneous or quasi-homogeneous phase keeping the nitrogen-containing organic templating agent as a distinctly separate phase. It is also possible to utilize the low impact agitation for short periods of time during the substantially static phase as opposed to continuously during that whole period.

It is preferred that the slurry of crystalline molecular sieve is maintained at a temperature below the crystallization temperature during the static period. Preferably the slurry is maintained at a temperature of less than 100° C., more preferably less than 45° C., and most preferably at or below room or ambient temperature. In a preferred embodiment the static period is undertaken without the application of heat to the slurry.

The static period is commenced after substantially complete crystallization, which may be taken to be any time after equilibrium has been established between molecular sieve crystal formation and molecular sieve dissolution. If the crystallization process is not in equilibrium due to the presence of additional process steps, which perturbate or drive the equilibrium in a particular direction, then substantially complete crystallization may be taken to be the point, during the crystallization process, at which a particular pre-determined yield of crystalline material has been achieved. The substantially static phase does not include the recovery stage of the process. Recovery stages may require static conditions e.g. when flocculation is used, such static conditions do not correspond with the substantially static phase as used in the process of the present invention.

The substantially static phase may be for any extended period of time after substantial completion of the crystallization up to the recovery stage. The static phase may be from 1 to 480 hours, preferably a period from 2 to 240 hours, and most preferably a period from 5 to 240 hours.

In another embodiment, in addition to the slurry being maintained under static conditions, at least a portion of the nitrogen-containing organic templating agent may be removed from the slurry at the start of or during the substantially static phase. It has been found that the combination of static conditions combined with the removal of at least a portion of the nitrogen-containing organic templating agent at the start of or during the substantially static phase, results in a further improvement in the yield of crystalline molecular sieve on recovery after storage as the dissolution is further reduced.

In a further embodiment, in addition to the slurry being maintained under substantially static conditions, the pH of the slurry may be reduced at the start of or during the substantially static phase. This pH reduction may be undertaken in combination with removal of the nitrogen-containing organic templating agent. In one embodiment the pH reduction is achieved by removal of the nitrogen-containing organic templating agent.

The process of the present invention results in reduction in yields on storage of less than 40%, preferably less than 30% and more preferably less than 20%.

After storage, the molecular sieve can be recovered by any standard means, such as by centrifugation or filtration. The separated molecular sieve product can also be washed, recovered by centrifugation or filtration and dried.

As a result of the molecular sieve crystallisation process, the recovered molecular sieve contains within its pores at least a portion of the template. The crystalline structure essentially wraps around the template. If catalytic activity is desired, the template should be removed before catalytic use. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process is used for partial or complete removal of the template from the intracrystalline pore system. In other cases, particularly with smaller templates, complete or partial removal from the sieve can be accomplished by conventional desorption processes.

The process of the present invention for the manufacture of SAPO and/or ALPO crystalline molecular sieves results in products, which are useful in a number of applications including catalysis.

The present invention therefore also provides for a SAPO and/or ALPO molecular sieve obtainable by and preferably obtained by the process of the present invention which utilises storage under substantially static conditions.

The molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-18, etc., the metal containing forms thereof, and mixtures thereof. Preferably, the molecular sieve is selected from the group consisting of SAPO-18, SAPO-34, SAPO-35, SAPO-44, SAPO-47, ALPO-5, ALPO-11, ALPO-18, ALPO-31, ALPO-34, ALPO-36, ALPO-37, and ALPO-46, the metal containing forms thereof, and mixtures thereof. More preferably, the silicoaluminophosphate is selected from the group consisting of SAPO-18, SAPO-34, ALPO-18 and ALPO-34, the metal containing forms thereof, and mixtures thereof. The most preferred molecular sieve is SAPO-34. As used herein, the term mixture is synonymous with combination and is considered a composition of matter having two or more components in varying proportions, regardless of their physical state. In particular, it encompasses physical mixtures as well as intergrowths of at least two different molecular sieve structures; such as for example those described in PCT Publication No. WO 98/15496 and co-pending U.S. Ser. No. 09/924016.

SAPO and/or ALPO molecular sieves comprise a three-dimensional microporous crystal framework structure of $[SiO_2]$, $[AlO_2]$ and $[PO_2]$ tetrahedral units in the case of SAPOs and a three-dimensional microporous crystal framework structure of $[AlO_2]$ and $[PO_2]$ tetrahedral units in the case of ALPOs.

SAPO and ALPO molecular sieves are generally classified as being microporous materials having 8, 10, or 12 membered ring structures. These ring structures can have an average pore size ranging from about 3.5–15 angstroms. Preferred are the small pore SAPO and ALPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

The process of the present invention is also suitable for the preparation of substituted SAPOs and ALPOs. These compounds are known as MeAPSOs, ElAPSOs or metal-containing silicoaluminophosphates and MeAPOS, ElAPOs or metal-containing APOs. The metal can be an alkali metal (Group IA), an alkaline earth metal (Group IIA), a rare earth metal (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium), a and the additional transition metal cations of Groups IVB, VB, VIB, VIIB, VIIIB, and IB, or mixtures of any of these metal species.

Preferably, the metal is selected from the group consisting of Zn, Mg, Mn, Co, Ni, Ga, Fe, Ti, Zr, Ge, Sn, Cr, Cu and mixtures thereof. These metal atoms are inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is accomplished by adding the source of MeO$_2$ during synthesis of the molecular sieve. Accordingly, the present invention also relates to a process for the synthesis of crystalline molecular sieve wherein the molecular sieve is one or more silicoaluminophosphates (SAPO), and/or one or more aluminophosphate (ALPO) and mixtures thereof, in which the reaction mixture further comprises a source of MeO$_2$, in addition to the other ingredients, Me being preferably within the group consisting of Zn, Mg, Mn, Co, Ni, Ga, Fe, Ti, Zr, Ge, Sn, Cr, Cu and mixtures thereof.

MeAPSOs and MeAPOs prepared according to the present invention include those disclosed in U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,935,216 (ZnAPSO), U.S. Pat. No. 4,738,837 (CrAPSO), U.S. Pat. Nos. 4,759,919, 4,851,106 (CrAPO), U.S. Pat. Nos. 4,758,419, 4,882,038, 5,434,326, 5,478,787 (MgAPSO), U.S. Pat. Nos. 4,822,478, 4,683,217, 4,744,885 (FeAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956, 4,793,833 (MnAPSO), U.S. Pat. Nos. 5,345,011, 6,156,931 (MnAPO) U.S. Pat. No. 4,737,353 (BeAPSO), U.S. Pat. No. 4,940,570 (BeAPO), U.S. Pat. Nos. 4,801,309, 4,684,617, 4,880,520 (TiAPSO), U.S. Pat. Nos. 4,500,651, 4,551,236, 4,605,492 (TiAPO), U.S. Pat. Nos. 4,824,554, 4,744,970 (CoAPSO), U.S. Pat. No. 4,735,806 (GaAPSO), as well as U.S. Pat. Nos. 4,801,364, 4,853,197, 4,567,029, 4,686,093, 4,781,814, 4,952,384, 4,793,984, 4,973,785, 4,956,165, 4,917,876, 4,956,164, 5,493,066, 5,675,050, 5,241,093 (MeAPSOs and APOs with several possible metals in the framework, including metal mixtures) all fully incorporated herein by reference.

Once the molecular sieve is made, it can be formulated into a catalyst by combining the molecular sieve with other materials that provide additional hardness or catalytic activity to the finished catalyst product. When combined with these other materials, the resulting composition is typically referred to as a silicoaluminophosphate and/or aluminophosphate catalyst, with the catalyst comprising the SAPO and/or ALPO molecular sieve. This invention also relates to catalysts comprising the molecular sieves of this invention.

Materials which can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with various inert or catalytically active materials, or various binder materials, the amount of SAPO and/or ALPO molecular sieve prepared by the method of the invention which is contained in the final catalyst product ranges from 10 to 90 weight percent of the total catalyst, preferably 20 to 70 weight percent of the total catalyst.

The molecular sieves synthesized in accordance with the present method can be used to dry gases and liquids; for selective molecular separation based on size and polar properties; as ion-exchangers; as catalysts in cracking, hydrocracking, disproportionation, alkylation, isomerization, oxidation; as chemical carriers; in gas chromatography; and in the petroleum industry to remove normal paraffins from distillates.

The SAPOs and/or ALPOs of the present invention are particularly suited for the catalytic conversion of oxygenates to hydrocarbons. Accordingly, the present invention also relates to a method for making an olefin product from an oxygenate feedstock wherein said oxygenate feedstock is contacted with the catalyst of this invention comprising the molecular sieve of this invention under conditions effective to convert the oxygenate feedstock to olefin products. When compared to other SAPOs and/or ALPOs under the same operating conditions, the SAPOs and/or ALPOs of the present invention exhibit higher selectivity to light olefins, especially ethylene and propylene, and produce fewer by-products. Throughout this specification, the expression "light olefins" is intended to mean olefins having from 2 to 5 carbon atoms.

In this process a feedstock containing an oxygenate contacts a catalyst comprising the molecular sieve of the present invention in a reaction zone of a reactor at conditions effective to produce light olefin(s), particularly ethylene and/or propylene. Typically, the oxygenate feedstock is contacted with the catalyst containing the molecular sieve when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

In this oxygenate conversion process, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of light olefin.

An operating temperature of at least 300° C., and up to 525° C. is preferred.

In a preferred embodiment, it is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T-400)/400) \times 14.84)}$$

The pressure also may vary over a wide range, including autogenous pressures. Preferred pressures are in the range of about 5 kPa to about 5 MPa, with the most preferred range being of from about 50 kPa to about 0.5 MPa. The foregoing pressures are exclusive of any oxygen depleted diluent, and thus, refer to the partial pressure of the oxygenate compounds and/or mixtures thereof with feedstock.

The process can be carried out in a dynamic bed system or any system using a variety of transport beds, although a fixed bed system could be used. It is particularly desirable to operate the reaction process at high space velocities.

The process may be carried out in a batch, semi-continuous or continuous fashion. The process can be conducted in a single reaction zone or a number of reaction zones arranged in series or in parallel.

The conversion of oxygenates to produce olefins is preferably carried out in a large-scale continuous catalytic reactor. This type of reactor includes fluid bed reactors and concurrent riser reactors as described in "Free Fall Reactor," *Fluidization Engineering*, D. Kunii and O. Levenspiel, Robert E. Krieger Publishing Co. N.Y., 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems*, pages 48–59, F. A. Zenz and D. F. Othmo, Reinhold Publishing Corp., N.Y. 1960, the descriptions of which are fully incorporated herein by reference.

Any standard commercial scale reactor system can be used, for example fixed bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feedstock per hour per weight of SAPO and/or ALPO molecular sieve content of the catalyst. The hydrocarbon content is the oxygenate content and the content of any hydrocarbon which may be present with the oxygenate. The SAPO and/or ALPO molecular sieve content means only the SAPO and/or ALPO molecular sieve portion that is contained within the catalyst. This excludes components such as binders, diluents, inerts, rare earth components, etc.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The level of conversion of the oxygenates is maintained to reduce the level of unwanted by-products. Conversion is also maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is preferred. Therefore, conversion levels that achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion is maintained using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is used, the molecular sieve catalyst can be continuously introduced as a moving bed to a regeneration zone where it is be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound that contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof. The most preferred oxygenate compound is methanol.

The process for making an olefin product from an oxygenate feedstock by contacting the oxygenate feedstock with a catalyst comprising a SAPO and/or ALPO of the present invention has good catalytic performances. The selectivity to ethylene and propylene is equal to or greater than 75.0%; the ethylene to propylene ratio is equal to or greater than 0.75; the selectivity to propane is equal to or lower than 1.0%.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefin products made by the oxygenate-to-olefin conversion reaction using the molecular sieve of the present invention can be polymerized to form polyolefins, particularly polyethylenes and polypropylenes. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst as described in U.S. Pat. No. 5,324,800. The preferred temperature range of operation is between 50° C. and 240° C. and the reaction can be carried out at low, medium or high pressure, being anywhere within the range of about 1 to 200 bars (0.1 to 20 Mpa). For processes carried out in solution, an inert diluent can be used, and the preferred operating pressure range is between 10 and 150 bars (1 to 15 Mpa), with a preferred temperature range of between 120° C. and 230° C. For gas phase processes, it is preferred that the temperature generally be within a range of 60° C. to 160° C., and that the operating pressure be between 5 and 50 bars (0.5 to 5 Mpa).

In addition to polyolefins, numerous other olefin derivatives may be formed from the olefins recovered from this invention. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLES

Example 1

SAPO-34 was crystallized in the presence of TEAOH and DPA as nitrogen-containing templating agents. A mixture of the following mole ratio composition was prepared:

142.9 g of Condea Pural SB® (available from Condea, Hamburg, Germany) was mixed with 209.9 g of deionised water, to form a slurry. To this slurry was added 242.3 g of phosphoric acid (85%) and 167.5 g water; 41.3 g of water was used to rinse the container and also added to slurry. These additions were made with stirring to form a homogeneous mixture. To this homogeneous mixture 47.2 g of Ludox AS40 (available from E. I. du Pont de Nemours, Wilmington, Del.) was added together with 17.5 g of rinse water, followed by the addition of 441.9 g of a tetraethylammoniumhydroxide (TEAOH) solution (35 wt %, available from Eastern Chemical, Austin, Tex.) with mixing to form a homogeneous mixture. To this homogeneous mixture was added 170.1 g of dipropylamine (DPA) with 102.6 g of rinse water.

This homogeneous mixture was crystallized in a 2 liter Parr autoclave equipped with a stirrer. The mixture was stirred at 170 rpm and then heated to 175° C. in 8 hours. The mixture was stirred for a further 5 hours at 175° C. and 170 rpm. The stirring was stopped and the reaction mixture was maintained at 175° C. for a further 19 hours. This provided a slurry of crystalline molecular sieve.

On completion of the reaction the slurry containing SAPO-34 was cooled down to room temperature.

a) Sample A:

A first portion of the slurry (267.9 g) was washed by dispersing the slurry in water, centrifuging and decanting. This process was repeated until the conductivity of the supernatant was below 50 μS/cm. The washed slurry was then dried at 120° C. overnight, providing 33.1 g of dried SAPO-34 after recovery; this corresponds to a yield of 12.4%.

b) Sample B:

A second portion of the slurry (224.6 g) was then stored before recovery by maintaining the slurry at room temperature with stirring at 170 rpm for 72 hours. After storage the SAPO-34 was recovered in the in the same manner as for Sample A, and the yield of SAPO-34 was determined to be 6.6 wt %. It was also observed that the quality of the SAPO-34 crystals had deteriorated during storage in the slurry. The SEM (scanning electron microscopy) pictures of the crystals showed leached surfaces of the crystals. For fresh crystals, the surfaces were smooth.

After storage with stirring the reduction in yield compared to that achieved immediately after crystallization was 47% (yield of Sample B relative to yield of Sample A).

Example 2

Sample C:

SAPO-34 was crystallized in the presence of TEAOH and DPA as nitrogen-containing templating agents using the same ingredients and ingredient ratios as in Example 1. On completion of the reaction the slurry containing SAPO-34 was cooled down to room temperature. The slurry was then stored before recovery. In this example the slurry was stored at room temperature under completely static (un-stirred) conditions for 10 days. After storage the SAPO-34 crystals were recovered by the method described for Sample A and the yield of SAPO-34 was determined to be 8.1 wt %. This corresponds to a reduction in yield compared to that achieved immediately after crystallization of 22.7% (Yield of Sample C compared to that of Sample A). Sample C was obtained in a significantly higher yield than Sample B (storage for 3 days with stirring at 170 rpm) This Example illustrates that storage under static (un-stirred) conditions significantly increases the yield of SAPO-34 compared to storage under stirred conditions. The SEM pictures of the crystals showed much less deterioration at the surface of the crystals.

Example 3

Sample D:

Example 2 was repeated except that after the slurry of crystalline molecular sieve was cooled to room temperature, the pH of the slurry was reduced by removal from the reaction medium of the residual DPA.

This substantially DPA free slurry was stored at room temperature under static (un-stirred) conditions for 10 days. After storage the SAPO-34 crystals were recovered by the method described for Sample A and the yield of SAPO-34 was determined to be 10.2 wt %. This is a 17.7% decrease in yield compared to that obtained immediately after crystallization (Sample D compared to Sample A). This Example illustrates that storage under static (un-stirred) conditions coupled with reduction of the slurry pH by removal of residual nitrogen-containing organic templating agent results in a marked improvement in the SAPO-34 yield after storage.

What is claimed is:

1. A process for synthesizing a crystalline molecular sieve, the process comprising the steps of:
 a) forming a reaction mixture comprising a source of alumina, a source of phosphate, at least one nitrogen-containing organic templating agent, and optionally a source of silica;
 b) inducing crystallization of the crystalline molecular sieve from the reaction mixture to form a slurry, the slurry comprising the crystalline molecular sieve; and
 c) recovering the crystalline molecular sieve from the slurry, wherein during any period of time after substantial completion of the crystallization in step (b), and prior to the recovery step (c), the slurry is held under substantially static conditions.

2. The process according to claim 1 wherein the slurry of the crystalline molecular sieve is stored after substantial completion of the crystallization in step (b), and prior to the recovery step (c).

3. The process according to claim 1 wherein the slurry is held at a temperature of 100° C. or less.

4. The process according to claim 1 wherein the slurry is held at a temperature of 45° C. or less.

5. The process according to claim 1 wherein the slurry is held at or below room or ambient temperature.

6. The process according to claim 1 wherein the crystalline molecular sieve is one or more silicoaluminophosphates (SAPO), and/or one or more aluminophosphate (ALPO), and mixtures thereof.

7. The process according claim 1 wherein at least some of the at least one of the nitrogen-containing organic templating agent is removed during the crystallization step (b).

8. The process according to claim 7 wherein the nitrogen-containing organic templating agent is removed prior to holding the slurry under substantially static conditions.

9. The process according to claim 7 wherein at least some of the nitrogen-containing organic templating agent is removed during the substantially static period.

10. The process according to claim 1, wherein the reaction mixture has a pH that is reduced after the reaction mixture is placed under crystallization conditions in step (b).

11. The process according to claim 1, wherein the slurry has a pH that is reduced.

12. The process according to claim 1, wherein the slurry has a pH that is reduced after the slurry has been placed under substantially static conditions.

13. A process according to claim 1, wherein the slurry has a pH that is reduced by removing the nitrogen-containing organic templating agent.

14. The process according to claim 1, wherein the crystalline molecular sieve is selected from the group consisting of: SAPO-17, SAPO-18, SAPO-34, SAPO-35, SAPO-44, SAPO-47, ALPO-5, ALPO-11, ALPO-18, ALPO-34, ALPO-36, ALPO-37, ALPO-46, metal containing forms thereof, and mixtures thereof.

15. The process according to claim 1, wherein the crystalline molecular sieve is selected from the group consisting of: SAPO-34, SAPO-18, ALPO-18, and mixtures thereof.

16. The process according to claim 1, wherein the crystalline molecular sieve comprises SAPO-34.

17. The process according to claim 1, wherein the process further comprises the step of removing the nitrogen-containing organic templating agent from crystalline molecular sieve.

18. The process according to claim 1, wherein the process further comprises short periods of agitation under the substantially static conditions.

19. The process according to claim 1, wherein during the period of time after substantial completion of the crystallization step (b), and prior to the recovery step(c), the slurry is held under static conditions.

20. The process according to claim 1, wherein the reaction mixture formed in step (a) further comprises a source of $MO_2$, wherein M is selected from the group consisting of: Zn, Mg, Mn, Co, Ni, Ga, Fe, Ti, Zr, Ge, Sn, Cr, Cu, and mixtures thereof.

21. A catalyst comprising crystals of a crystalline molecular sieve prepared according to claim 19.

22. A method of making olefins comprising contacting a feedstock comprising at least one oxygenate in the presence of a catalyst comprising crystals of a molecular sieve prepared according to claim 19 and under conditions suitable to convert the oxygenate into olefins.

* * * * *